United States Patent
Mueller

(10) Patent No.: US 7,566,340 B2
(45) Date of Patent: Jul. 28, 2009

(54) SURGICAL THREADING DEVICE AND METHOD FOR USING SAME

(75) Inventor: Gregory Paul Mueller, Beverly Hills, CA (US)

(73) Assignee: Implicitcare, LLC, Beverly Hill, CA (US)

( * ) Notice: Subject to any disclaimer, the term of this patent is extended or adjusted under 35 U.S.C. 154(b) by 457 days.

(21) Appl. No.: 11/566,618

(22) Filed: Dec. 4, 2006

(65) Prior Publication Data

US 2008/0132947 A1    Jun. 5, 2008

(51) Int. Cl.
*A61B 17/04* (2006.01)

(52) U.S. Cl. .................. 606/233; 606/232

(58) Field of Classification Search ......... 606/232–233, 606/18, 215–217, 228; 289/1.15; 623/15.12; 128/898
See application file for complete search history.

(56) References Cited

U.S. PATENT DOCUMENTS

| | | | | |
|---|---|---|---|---|
| 1,358,753 | A * | 11/1920 | Killam et al. ............ | 24/713.1 |
| 5,222,508 | A * | 6/1993 | Contarini .................. | 128/898 |
| 5,391,156 | A | 2/1995 | Hildwein | |
| 5,391,175 | A | 2/1995 | Sharpe | |
| 5,728,103 | A * | 3/1998 | Picha et al. ............... | 606/108 |
| 5,769,791 | A | 6/1998 | Benaron | |
| 5,797,929 | A | 8/1998 | Andreas | |
| 5,879,306 | A | 3/1999 | Fontenot | |
| 5,951,543 | A | 9/1999 | Brauer | |
| 6,029,323 | A * | 2/2000 | Dickie et al. ............. | 24/712.6 |
| 6,152,951 | A | 11/2000 | Hashimoto | |
| 6,162,211 | A | 12/2000 | Tankovich | |
| 6,245,091 | B1 | 6/2001 | Buncke | |
| 6,391,023 | B1 * | 5/2002 | Weber et al. ............. | 606/15 |
| 6,432,101 | B1 * | 8/2002 | Weber et al. ............. | 606/2 |
| 6,432,970 | B2 * | 8/2002 | Beachy et al. ........... | 514/278 |
| 6,500,184 | B1 | 12/2002 | Chan | |
| 6,663,618 | B2 * | 12/2003 | Weber et al. ............. | 606/2 |
| 6,945,777 | B2 | 9/2005 | Black | |
| 6,974,450 | B2 * | 12/2005 | Weber et al. ............. | 606/2 |
| 7,048,682 | B2 | 5/2006 | Neisz | |
| 7,060,079 | B2 | 6/2006 | Wulc | |
| 7,494,488 | B2 * | 2/2009 | Weber ....................... | 606/2 |
| 2001/0025190 | A1 * | 9/2001 | Weber et al. ............. | 607/89 |

(Continued)

OTHER PUBLICATIONS

Declaration under 37 CFR 1.56 of Gregory Mueller describing a procedure that was used more than one year prior to the filing date of the referenced application. The Examiner is invited to contact applicant's attorney should he/she have any questions regarding the declaration.

(Continued)

*Primary Examiner*—(Jackie) Tan-Uyen T Ho
*Assistant Examiner*—Son Dang
(74) *Attorney, Agent, or Firm*—Jeffer Mangels Butler & Marmaro, LLP

(57) ABSTRACT

A threading device that includes an elongated tube having first and second opposite ends and a fiberoptic core. The elongated tube includes an interior and an eyelet defined therein. The first end of the elongated tube includes a blunt tip affixed thereto and the second end includes a threaded connector. The blunt tip is translucent. The fiberoptic core includes at least one fiberoptic strand extending through the interior of the elongated tube that illuminates the translucent tip when the at least one fiberoptic strand is energized.

12 Claims, 13 Drawing Sheets

U.S. PATENT DOCUMENTS

| | | |
|---|---|---|
| 2002/0019670 A1* | 2/2002 | Crawley et al. ........... 623/11.11 |
| 2002/0029011 A1* | 3/2002 | Dyer ........................... 602/41 |
| 2002/0064302 A1* | 5/2002 | Massengill .................. 382/128 |
| 2002/0198544 A1* | 12/2002 | Uflacker ..................... 606/144 |
| 2003/0014041 A1* | 1/2003 | Weber et al. .................... 606/2 |
| 2004/0002735 A1 | 1/2004 | Lizardi |
| 2004/0122451 A1 | 6/2004 | Wood |
| 2004/0133216 A1 | 7/2004 | Wulc |
| 2004/0167574 A1* | 8/2004 | Kuyava et al. ............... 606/224 |
| 2004/0267314 A1* | 12/2004 | Wolf et al. .................. 606/230 |
| 2004/0267315 A1* | 12/2004 | Wolf et al. .................. 606/230 |
| 2005/0055073 A1* | 3/2005 | Weber .......................... 607/99 |
| 2005/0099824 A1 | 5/2005 | Dowling |
| 2005/0203576 A1 | 9/2005 | Sulamanidze |
| 2005/0256535 A1 | 11/2005 | Capurro |
| 2005/0267531 A1* | 12/2005 | Ruff et al. ................... 606/228 |
| 2005/0267532 A1* | 12/2005 | Wu .............................. 606/228 |
| 2006/0079935 A1 | 4/2006 | Kolster |
| 2006/0095103 A1 | 5/2006 | Eggers |
| 2006/0293555 A1 | 12/2006 | Salter |
| 2009/0082791 A1* | 3/2009 | Schroeder et al. ........... 606/151 |

OTHER PUBLICATIONS

Ishizaka, Kazuhiro et al., "A Light-Guide Needle for Subureteric Injection of Materials to Treat Vesicoureteral Reflux (VUR)", Department of Urology, Tokio Medical and Dental University School of Medicine, Tokyo, Japan, Engineering & Urology Society, 14th Annual Meeting (May 1999).

* cited by examiner

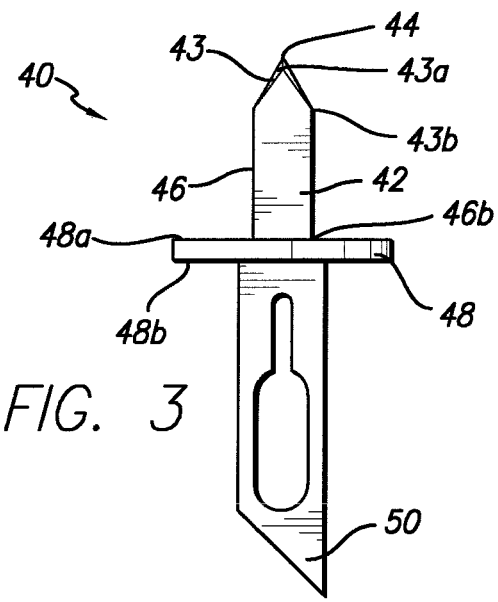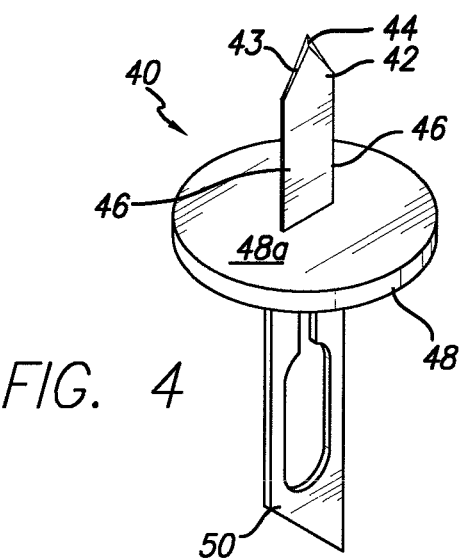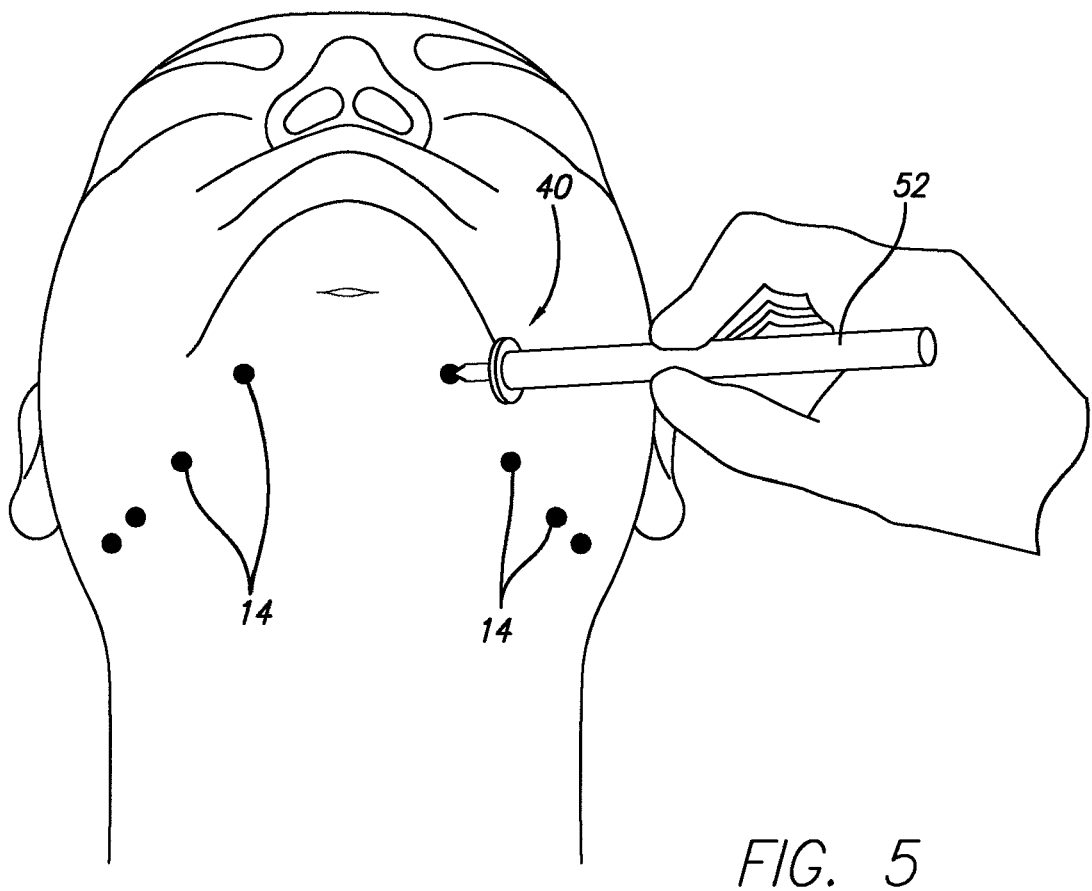
FIG. 3
FIG. 4
FIG. 5

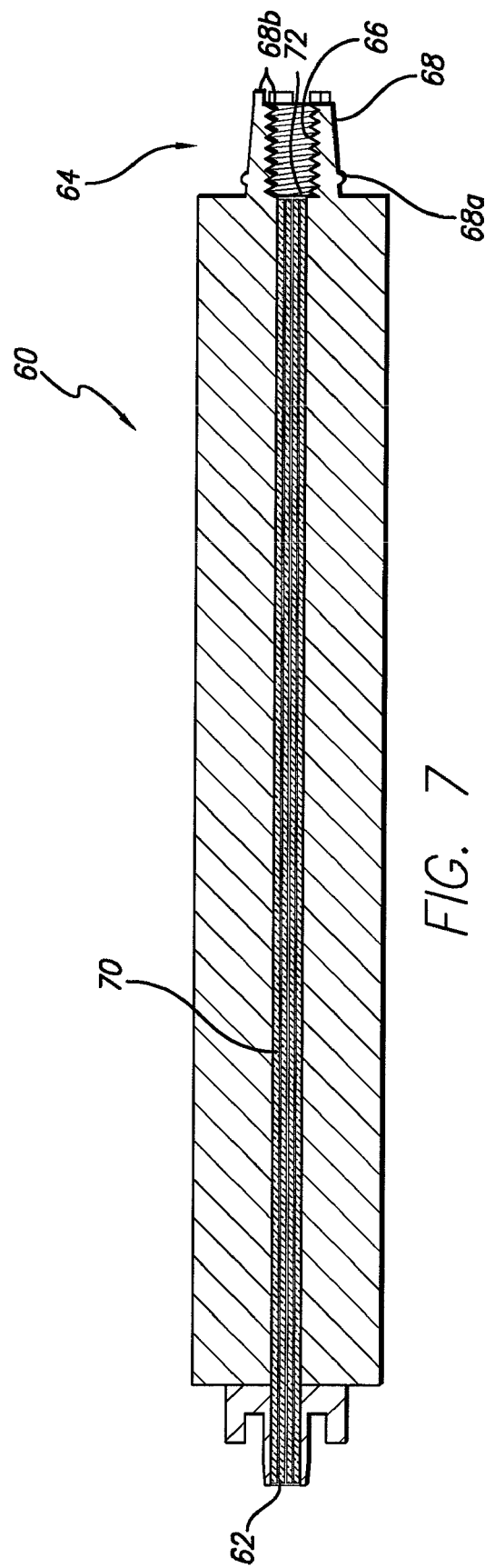
FIG. 6
FIG. 7

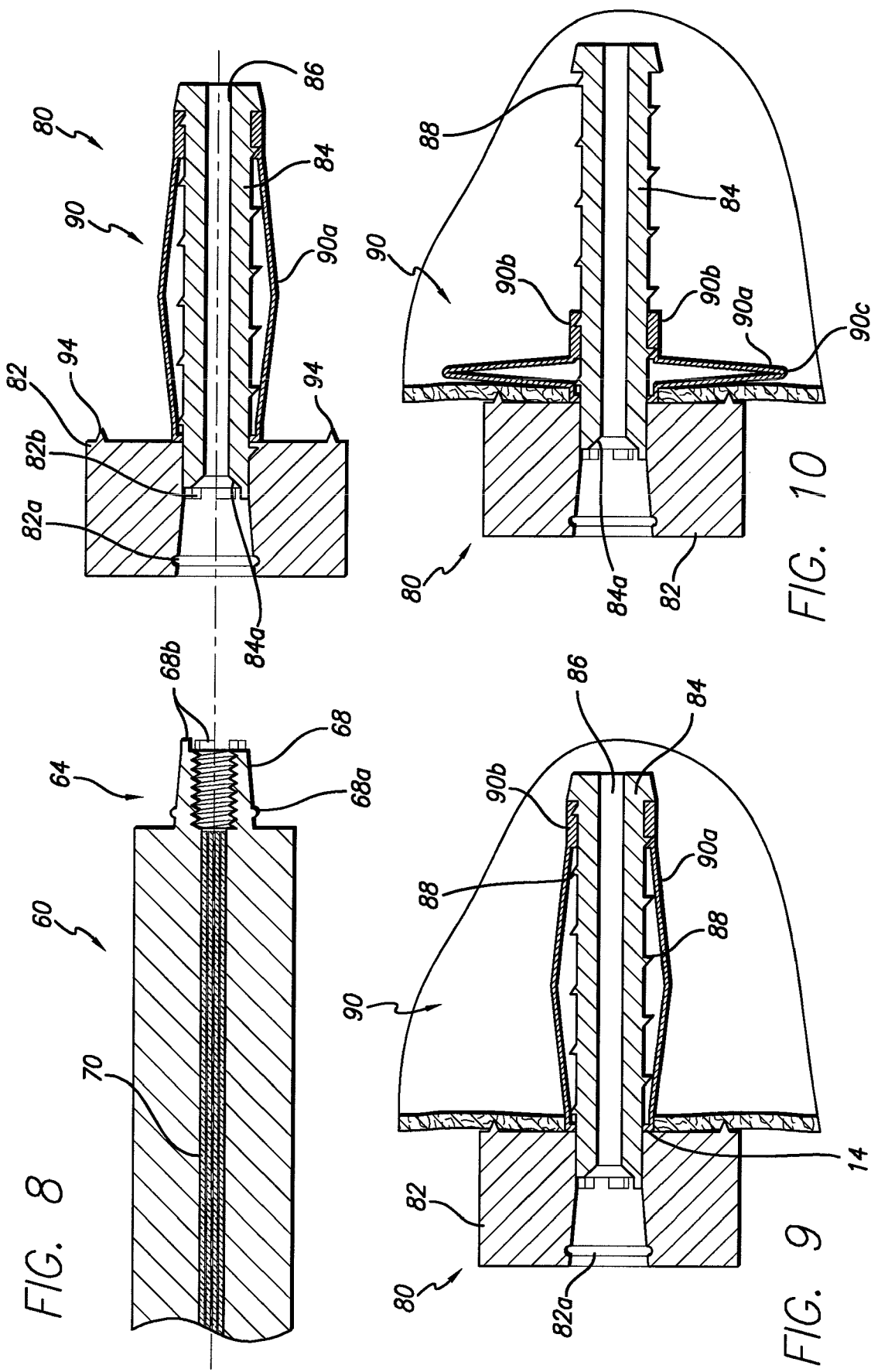

1

SURGICAL THREADING DEVICE AND METHOD FOR USING SAME

FIELD OF THE INVENTION

The present invention relates generally to methods and devices for plastic surgery and, more particularly, to a necklift procedure that is minimally invasive and to instruments for performing the procedure.

BACKGROUND OF THE INVENTION

Conventional neck rejuvenation surgeons advocate procedures that alter the anatomy of the neck to restore a more youthful neck contour. These involve platysmal manipulation such as muscle advancement and/or division, and frequently sub-platysmal fat excision. Partial resection of submandibular gland tissue may be performed as well. These techniques vary in complexity and may result in significant complications, including post-operative bleeding, nerve injury, permanent visible skin deformities caused by muscle division, or over-resection of fat.

Plastic and reconstructive surgeons have long sought to develop methods and devices to aid in the support of physical structures that have lost their natural tension and support. The most often treated areas include the face, the chest region, the buttocks and other regions that lose tension and sag. Current devices are not always adequate in providing a natural-looking structure to prevent such loss of tension in these structures.

The aging process causes gradual and predictable changes in the soft tissue layers of the lower face and neck, the anatomical basis of which has been well documented. Loss of elasticity and fragmentation of collagen results in rhytid formation and skin redundancy. Subcutaneous fat thickens and droops or is ptotic and becomes more noticeable. Stretching of the fascia and musculature results in a loss of the supporting 'sling' of the submentum, often resulting in submandibular gland ptosis. Further loss of tone and muscular atrophy results in banding of the medial platysmal borders, blunting of the cervicomental angle and loss of lateral mandibular definition.

The classical necklift's failure in adequately addressing the consequences of aging in the neck has prompted the development of a number of modifications and adjunctive procedures. These include skin excisions, various lipoplasty techniques, anterior or posteriorly based platysmal transection, resection, or plication procedures, SMAS-platysma flaps, and even suture suspension techniques. However, these modifications have their limitations.

Problems with scar contractures and hypertrophic scarring have resulted in the near abandonment of midline skin excision with subsequent Z, W or T-plasty. Liposuction or direct lipocontouring plays an important role in the aging neck.

SUMMARY OF THE PREFERRED EMBODIMENTS

In accordance with a first aspect of the present invention, there is provided a method of creating a suture support matrix under the skin of a person. The method includes the steps of connecting a threading device to the first end of a suture, inserting the threading device through a first opening in the skin, pulling the threading device through a second opening in the skin, reinserting the threading device through the second opening in the skin, pulling the threading device through a third opening in the skin, reinserting the threading device through the third opening in the skin, pulling the threading device through a fourth opening in the skin, disconnecting the threading device from the first end of the suture, connecting a threading device to the second end of the suture, inserting the threading device through the first opening in the skin, pulling the threading device through a fifth opening in the skin, reinserting the threading device through the fifth opening in the skin, pulling the threading device through the fourth opening in the skin, disconnecting the threading device from the second end of the suture, and tying the first and second ends of the suture into a knot. The threading device includes an elongated main body portion having first and second opposite ends. The second end of the elongated main body portion is connected to the first end of the suture.

In preferred embodiments, the first, second, third, fourth and fifth openings include skin ports inserted therein through which the threading device is inserted, and the threading device includes fiberoptic core that lights its tip. In another preferred embodiment, the threading device is connected to a handset before being inserted through the first opening in the skin, and the threading device is disconnected from the handset after at least a portion of the threading device has been pulled through the second opening in the skin.

In accordance with another preferred embodiment of the present invention, there is provided a threading device that includes an elongated tube having first and second opposite ends and a fiberoptic core. The elongated tube includes an interior and an eyelet defined therein. The first end of the elongated tube includes a blunt tip affixed thereto and the second end includes a threaded connector. The blunt tip is translucent. The fiberoptic core includes at least one fiberoptic strand extending through the interior of the elongated tube that illuminates the translucent tip when the at least one fiberoptic strand is energized.

BRIEF DESCRIPTION OF THE DRAWINGS

The invention may be more readily understood by referring to the accompanying drawings in which:

FIG. 3 is a front elevational view of a lancet in accordance with a preferred embodiment of the present invention;

FIG. 4 is a perspective view of the lancet of FIG. 3;

FIG. 5 is a view of the lancet of FIG. 3 being used to make a puncture;

FIG. 6 is a side elevational view of a handset in accordance with a preferred embodiment of the present invention;

FIG. 7 is a sectional side elevational view of the handset of FIG. 5 showing the fiberoptic core;

FIG. 8 is a cross-sectional view of the handset of FIG. 5 before docking with a skin port in accordance with a preferred embodiment of the present invention;

FIG. 9 is a cross-sectional view showing the skin port inserted through a patient's skin before deployment;

FIG. 10 is a cross-sectional view showing the skin port inserted through a patient's skin after deployment;

Like numerals refer to like parts throughout the several views of the drawings.

DETAILED DESCRIPTION OF THE PREFERRED EMBODIMENTS

Described herein are preferred embodiments of a technique for plastic surgery (e.g., liposuction to a person's chin or jaw area) that only uses one small incision. The technique involves several steps which each require specific instrumentation. The technique is referred to herein as Percutaneous Trampoline Platysmaplasty.

The liposuction portion of the procedure is performed without a large incision under the chin. The placement of the suture support matrix is performed through several small access sites in the neck area under the jaw. The advantage is that the entire support system can be placed without the typical large incision under the chin that is necessary for the surgeons to see the operative field. In addition the surgery is less invasive and does not require an extensive dissection of the skin in the area under the chin.

Figure 25:
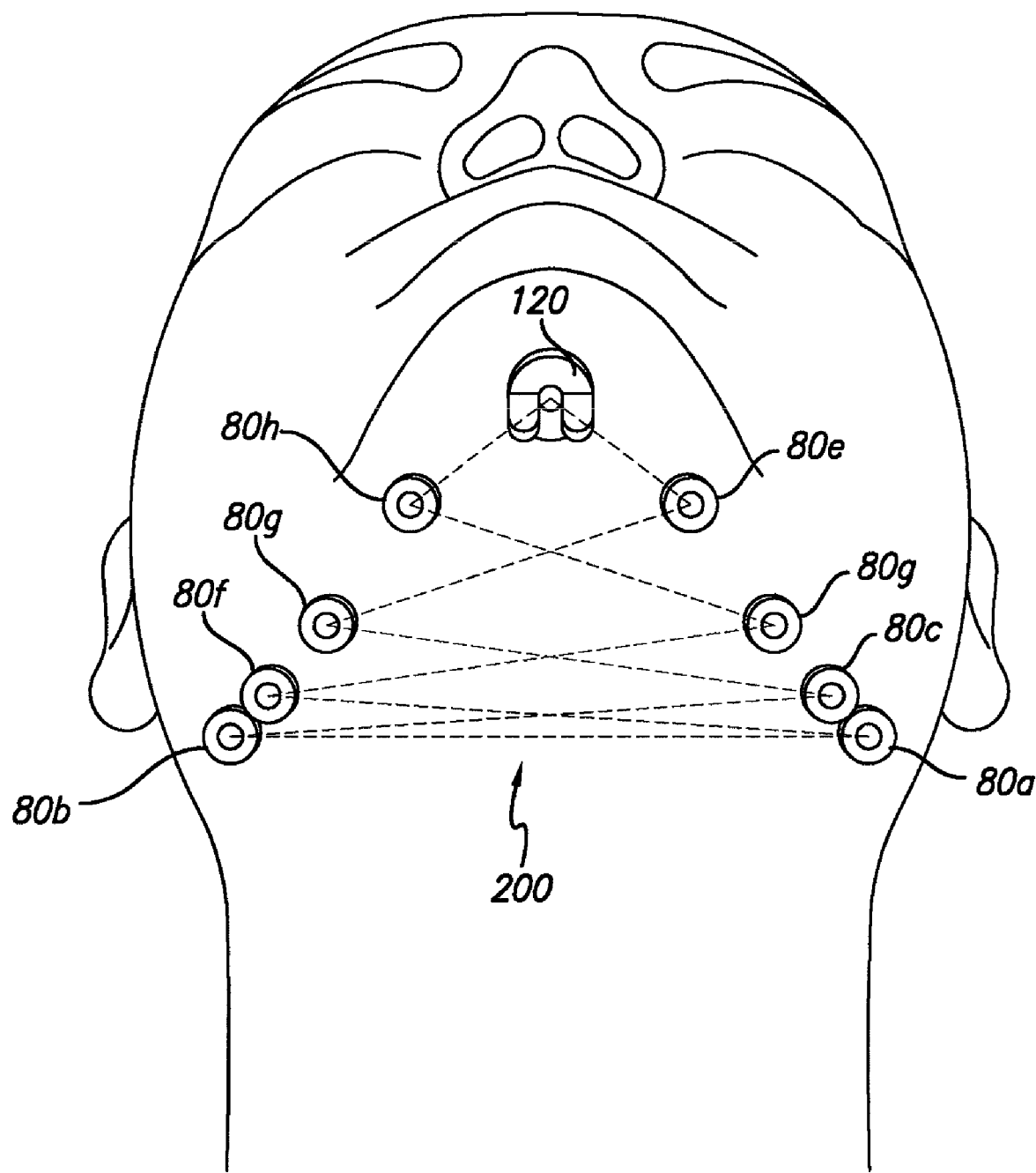
FIG. 25 is a view of a patient with the support matrix shown in hidden lines.

The accurate placement of the support suture (also referred to herein as the support structure or support matrix 200 and is shown in FIG. 25) will be described herein along with the description of each of the individual instruments or devices that may be used in connection with such procedure.

As described above, the inventive aspects of the present invention involve the placement of the support matrix 200 and not the actual liposuction technique. Therefore, it will be understood that any references to liposuction techniques herein are only exemplary.

It will be appreciated that terms such as "front," "back," "top," "bottom," "side," "upwardly" and "downwardly" used herein are merely for ease of description and refer to the orientation of the components as shown in the figures. It should be understood that any orientation of the instruments and articles and the components thereof described herein is within the scope of the present invention.

Figure 1:
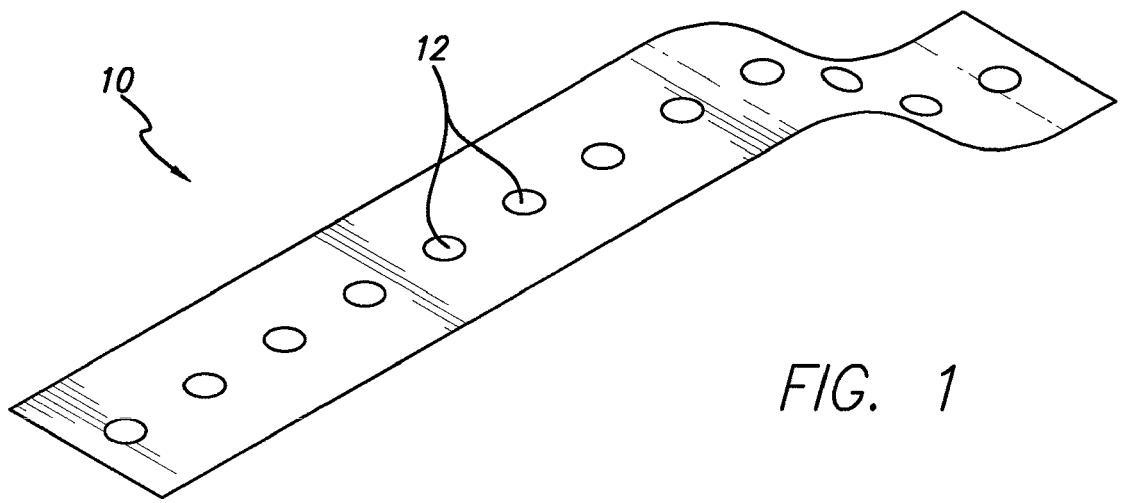
FIG. 1 is a perspective view of a tape template in accordance with a preferred embodiment of the present invention.
Figure 2:
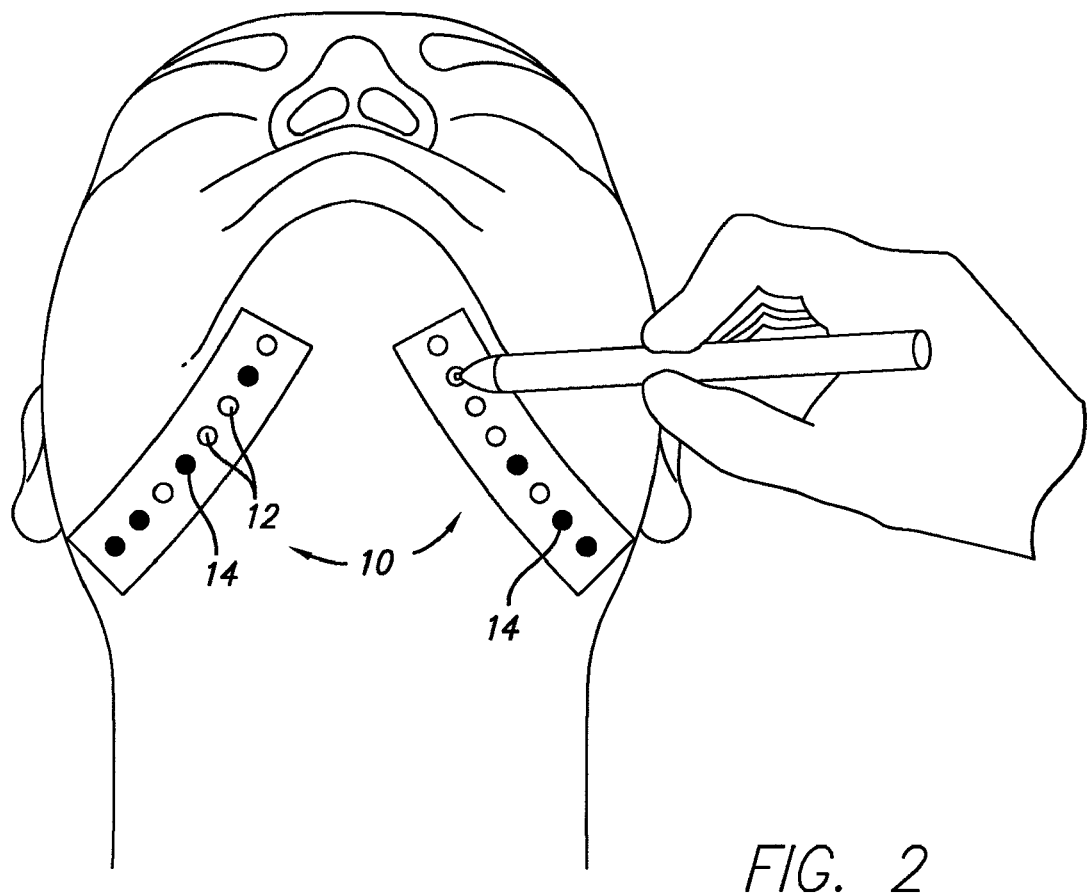
FIG. 2 is a view of the tape template of FIG. 1 being used to mark puncture locations on a patient's chin.

Referring to FIGS. 1-2, template tape (or tape members) 10 will be described. In a preferred embodiment, tape 10 is a clear piece of tape with perforations 12 therethrough that are spaced apart at predetermined locations. Tape 10 includes adhesive thereon so that it can be secured to the patient's skin. In an exemplary embodiment, tape 10 is a one inch wide clear tape with about 2 mm circular perforations 12 defined therethrough that are spaced about every 5 mm along the center of the tape. The perforations 12 are preferably positioned along the longitudinal center of the tape 10, however this is not a limitation on the present invention. In another embodiment, tape 10 is not clear. In a preferred embodiment, tape 10 is provided in roll form. However, this is not a limitation on the present invention.

Tape 10 is used in immediate pre-operative planning to determine the placement of access sites 14, which will determine the placement of the support matrix 200. Tape 10 is used as a guide to help provide proper placement of each suture and its corresponding pivot point (as described below). Perforations 12 are used to mark access sites for the surgery.

In a preferred embodiment, first and second tape members 10 are placed on each side of the skin overlying the undersurface of the mandible, as is shown in FIG. 2. Preferably, tape 10 is utilized with the patient sitting upright, which allows the natural neck contours to be visible. This is not a limitation on the present invention, however. The surgeon uses tape 10 and the plurality of perforations 12 to develop a surgical approach that is individually tailored for each patient, depending on the correction desired. As those skilled in the art will appreciate, placement of the support matrix 200 will be different for different patients depending on the patient's anatomy.

The exemplary 5 mm span between perforations 12 allows placement of pivot points in close proximity. This results in a dense support matrix allowing elevation of muscle and glandular tissue. For example, pivot points may be placed 1-2 cm apart if minimal support is needed. Those skilled in the art will be able to make determinations as to where the access sites 14 should be located based on the patient's needs. For example, as is shown in FIG. 2, the surgeon has only chosen four access sites 14 on each side.

As shown in FIG. 2, after the tape 10 has been placed and the surgeon has determined the structure of the support matrix 200, the surgeon marks skin exposed through the desired perforations 12 with a surgical marking pen or the like. These markings 14 indicate the areas that require suture placement to elevate the soft tissue of the neck. In a preferred embodiment, as is shown in FIGS. 2 and 5, the markings 14 made using the first tape member 10 are symmetrical to the markings 14 made using the second tape member 10.

As will be described below, each of the markings 14 define a location or access site that will be punctured to allow subcutaneous access at that location. For simplicity, because each access site is marked and then punctured, the access sites, markings and punctures will all be labeled 14 herein.

As will be appreciated by those skilled in the art, in areas where significant platysmal banding or glandular ptosis is evident significant support will be required. To achieve this, multiple suture strands will be required. As each area to be elevated is recognized, a corresponding tape perforation 12 is marked 14 to insure that suture placement is accurate.

It will be understood that tape 10 is preferably used before performing liposuction. However, this is not a limitation on the present invention. In another embodiment, tape 10 can be used after liposuction is performed. In another embodiment, the tape 10 can be omitted and the surgeon can mark or puncture the skin as desired.

It will appreciated by those skilled in the art that the tape 10 can be used on areas of the body other than the chin. For example, the tape (and the remainder of the procedure described below) can be used for a cheek lift.

After the desired markings 14 have been made, the patient and draped in a sterile fashion and local anesthetic is injected into the area under the chin. A small opening (referred to herein as the midline sub-mental access site) is made in this area. Tumescent fluid is injected into the entire area under the chin, including the neck region. Liposuction is performed on the entire region. Upon completion, the area is once again infiltrated with the tumescent fluid. This subcutaneous infusion results in the elevation of the skin from the platysma muscle.

With reference to FIGS. 3-5, after completion of liposuction, the patient is ready for placement of the support matrix 200. A lancet 40 is used to create access sites 14 by puncturing the dermis at the points marked using tape 10.

As shown in FIG. 3, lancet 40 includes a blade 42 that has two sharp edges 43 that end at a point 44 with two blunt edges 46 therebelow. In a preferred embodiment, blade 42 is about 8 mm in length. Blunt edges 46 of blade 42 extend from a flange or stop member 48 that prevents blade 42 from going deeper into the skin than desired. Flange 48 ensures consistent depth of blade penetration. Also, blade 42 is sized to allow placement of skin ports 80 as described below.

Stop member 48 has an upper surface 48a and a lower surface 48b. The blade 42 extends upwardly from the upper surface 48a of the stop member 48. As is shown in FIG. 3, the two sharp edges 43 each have first and second ends 43a and 43b, respectively and the two blunt edges 46 each have first and second ends 46a and 46b, respectively.

In a preferred embodiment, the first ends 43a of the sharp edges 43 meet at point 44 and extend downwardly from point 44 at an angle of 90° or less. The first ends 46a of the two blunt edges 46 extend downwardly from the second ends 43b of the two sharp edges 43. The sharp edges 43 and blunt edges 46 meet at an obtuse angle. The second ends 46b of the two blunt edges 46 are connected to the stop member 48, which, in a preferred embodiment, is disc-shaped. However, this is not a limitation on the present invention. In an alternative embodiment, the blade 42 can extend from the stop member 48 at a non-right angle (e.g., an acute angle).

In a preferred embodiment, lancet 40 includes an attachment member 50 that extends downwardly from the lower surface 48b of the stop member 48 and allows the lancet 40 to be secured on a standard scalpel handle 52. In another embodiment, lancet 40 can be provided with a unitary handle.

The subcutaneous infusion described above results in the elevation of the skin from the platysma muscle. Once infiltrated, the access sites 14 are developed by puncturing of the skin with the percutaneous lancet 40 at the markings developed using tape 10, as shown in FIG. 5. Lancet 40 allows puncturing of the skin in order to gain access to the neck region and preferably ensures that each access site is as small as possible, allowing the placement of the support system 200.

It will be understood that in a preferred embodiment, lancet 40 creates punctures instead of incisions, which minimalizes trauma and the risk of scarring. However, incisions can be used in another embodiment.

Referring to FIGS. 6-7, the next instrument used in the procedure is a handset or handle 60. Handset 60 is embodied in a reusable insertion device with an instrument dock 64 at an end thereof. In a preferred embodiment, handset 60 also includes a fiber-optic light port 62. In a preferred embodiment, the handset is ergonomically designed to fit into the surgeon's hand when gripped. However, this is not a limitation on the present invention. Preferably, handset 60 is made of a metal, such as stainless steel or titanium. However, it can be made of other materials, such as a plastic or the like. As is described below, instrument port 64 is compatible with a number of the instruments that are used in the inventive surgical procedure. The design structure and form allows right to left hand interchangability with ease and precision.

In a preferred embodiment, instrument dock 64 includes an inner threaded surface or threaded female connector 66 and a larger male connector 68 that interlocks with the skin ports 80 (described below) allowing deployment and illumination. The instrument dock 64 is adapted to dock with certain instruments, as will be described more fully below. Handset 60 will be described more fully below in conjunction with the instruments with which it is intended to be used.

The fiberoptic light port 62 allows docking with a fiberoptic light cord (not shown). The transmission of fiberoptic light through the handset 60 illuminates each device when it is attached to the working end or instrument dock 64.

In a preferred embodiment, the handset 60 includes a fiberoptic core 70, which is made up of at least one, and preferably a plurality, of fiberoptic strands. When a fiberoptic light cord is connected to light port 62, the light is transmitted through the fibers and out through an opening 72 that is coaxial with female connector 66.

In another embodiment other types of lighting can be used. For example, LED, incandescent, fluorescent and other light sources can be used. However, it will be understood that the light transmission is not a limitation on the invention. The handset 60 (and associated instruments) can be provided without a fiberoptic core.

FIGS. 8-11 show a skin port 80. In a typical procedure, a plurality of skin ports 80 are used. In a preferred embodiment, skin ports 80 are disposable clear plastic sleeves that are each inserted into one of the access sites 14 created by lancet 40.

Generally, skin port 80 includes a flange or cuff 82 that has a tube 84 that extends from it. One end of the tube or sleeve 84 is inserted into the puncture 14 in the skin until the flange 82 rests against the outer surface of the skin. The flange 82 and tube 84 cooperate to define a tunnel 86 that will provide access to the area under the skin. Preferably, the port 80 is comprised of colored clear plastic. However, the port 80 in can also be made of other materials, does not have to be clear and does not have to be colored.

In a preferred embodiment, the handset 60 is used to deploy each port 80 through the individual access sites 14. Preferably, the skin ports 80 come in a kit, however this is not a limitation on the present invention. The handset 60 design allows quick interlocking with the skin port 80 to remove it from the kit. It will be understood that any design that allows the handset 60 to interlock with or engage the skin port 80 so that it can be deployed into the access site 14 is within the scope of the present invention.

In a preferred embodiment, the port 80 is snap fit onto the male connector 68. For example, as shown in FIG. 8, the male connector 68 can include a ridge 68a extending circumferentially therearound that cooperates with an indented ring 82a in the flange 82. The ridge 68a and indented ring 82a provide a snap fit so that the port 80 is engaged with the male connector 68 of the handset 60. Other snap fit arrangements are contemplated.

The tube 84 is then inserted through the access site 14. As shown in FIGS. 8-11, in a preferred embodiment, the skin port 80 includes an anchor system that comprises threads 88 on the outer surface of the tube 84 and a folding mechanism 90. The folding mechanism 90 preferably includes a pair of folding members 90a that are attached to an internally threaded ring 90b that moves up and down the tube 84 on threads 88.

Figure 11:
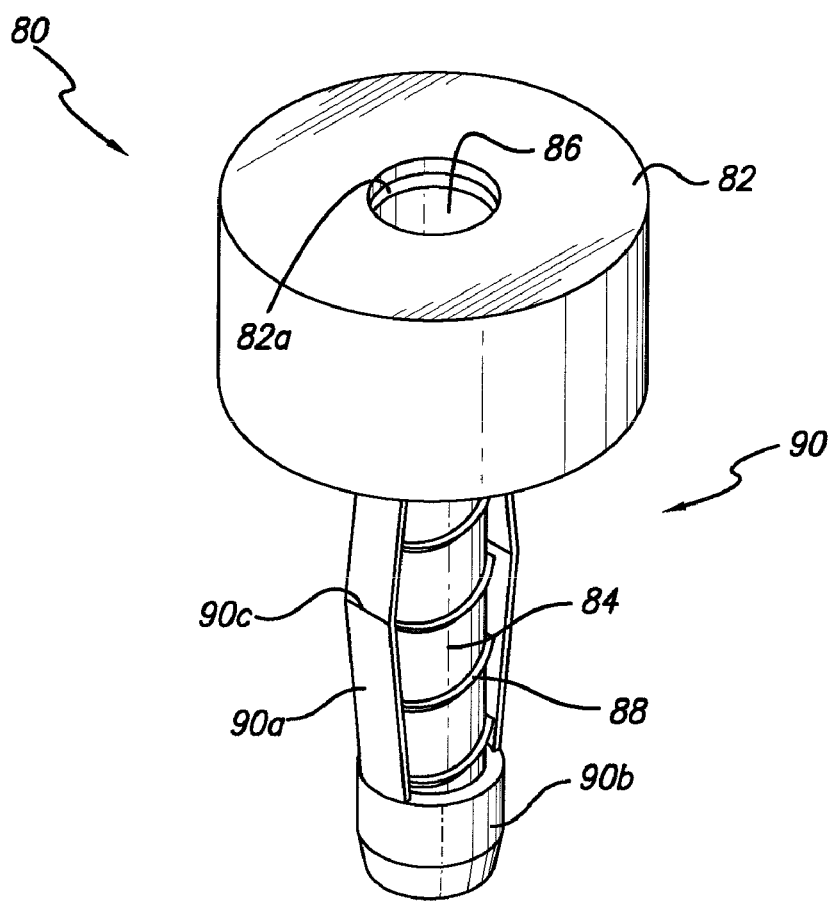
FIG. 11 is a perspective view of the skin port.

As is shown in FIG. 8, the male connector 68 includes a plurality of teeth 68b on an end thereof that are adapted to interlock with teeth 82b on the port 80. When the port 80 is engaged with the instrument dock 64, teeth 68b engage or mesh with teeth 82b. After the tube 84 has been inserted through the access site 14, to deploy the folding mechanism 90, the handset 60 is turned in a clockwise direction (port 80 can be designed to deploy in a counter-clockwise direction as well). Because teeth 68b and 82b are engaged, the tube 84 turns with handset 60 and within flange 82, thereby causing the internally threaded ring 90b to move upwardly along threads 88. As can be seen in FIG. 11, folding members 90a include a fold crease 90c. As threaded ring 90b moves upwardly, the folding members 90a fold, as shown in FIG. 10, thereby providing an anchor and preventing port 80 from pulling out of access site 14. The folding members 90a can be disposed in an unfolded position (FIG. 9) and a folded position (FIG. 10).

In a preferred embodiment, flange 82 includes a plurality of spikes 94 extending downwardly therefrom that burrow into the skin and help anchor the port 80 in place.

During placement of the port 80, because the handset 60 includes the fiber optic core 70 and the skin port 80 is clear, upon insertion, transcutaneous visualization of the lighted probe tip will allow safe deployment of skin port 80. Because of the anchoring system, as the handset is withdrawn, the ridge 68a pulls out of the indented ring 82a and the skin port 80 is secured in place. In another embodiment the surgeon can use his/her thumb to aid in separating the port 80 from the instrument dock 64.

Preferably, the ports 80 are disposable and are only used for a single surgery. It will be understood that the ports are simply used to gain access to the surgical field. Therefore, the type of port used is not a limitation on the present invention. Any type of port that provides access through the skin is within the scope of the present invention. The transillumination of light gives three dimensional feedback to the surgeon.

Figure 12:
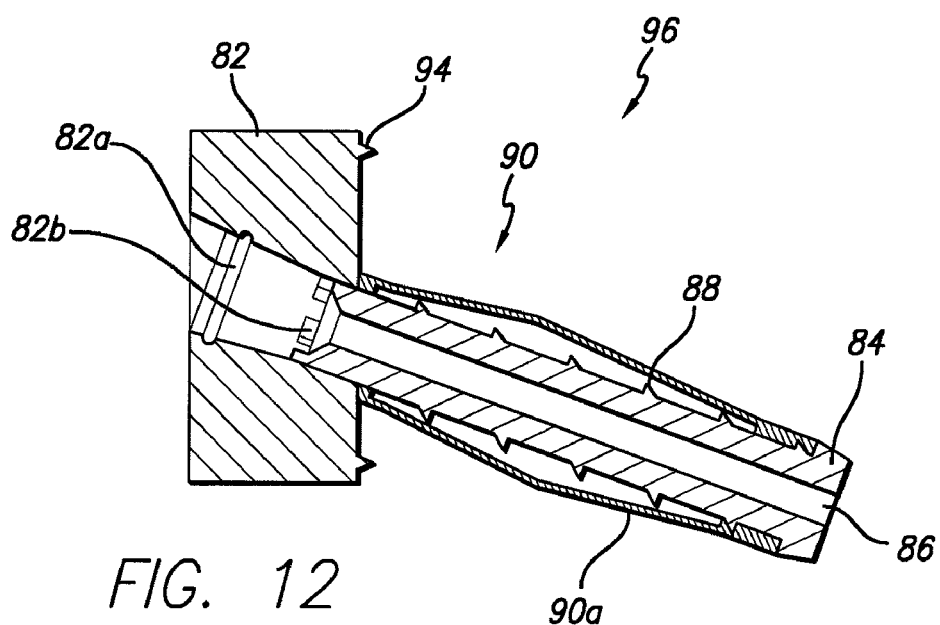
FIG. 12 is a cross-sectional view of another embodiment of a skin port.
Figure 13:
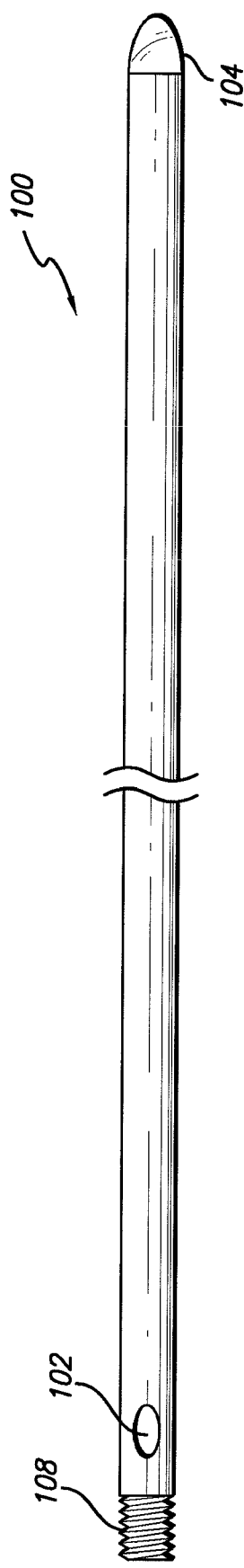
FIG. 13 is a side elevational view of a threading device in accordance with a preferred embodiment of the present invention.
Figure 14:
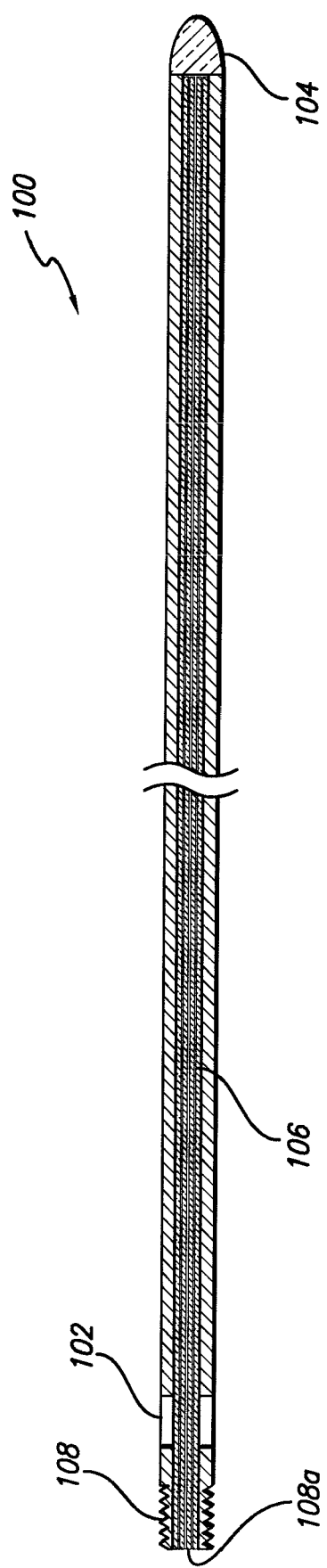
FIG. 14 is a sectional side elevational view of the threading device of FIG. 13.

As shown in FIG. 12, in an alternative embodiment, port 96 can have a tube 84 that is oriented at a non-right angle with respect to the flange 82. For example, tube 84 can be oriented at a 45 degree angle with respect to the flange.

FIGS. 13-17 show a threading device 100. In a preferred embodiment, threading device 100 is a stainless steel malleable rod or tube that includes an eyelet 102 defined therein and a rounded, blunt tip 104. Preferably, threading device 100 also includes a fiberoptic core 106 allowing illumination of tip 104. In this embodiment, the tip 104 is preferably made of a translucent material, such as a plastic that is affixed to the main body of the threading device 100. Threading device 100 includes an end 108 that is designed to dock with instrument dock 64 of handset 60. In a preferred embodiment, end 108 is threaded for engagement with female connector 66, however, it will be appreciated that end 108 can dock with instrument dock 64 in a number of different ways. For example, instrument dock 64 can include a set screw that holds threading device 100 in place or some type of snap or press fit can be provided. In another embodiment, a clamp or chuck, similar to that on a drill can be used. Also, end 108 can be internally threaded and can dock with an externally threaded instrument dock. Instrument dock 64 allows quick connection and disconnection with threading device 100.

In an embodiment where handset 60 includes a fiber-optic light port 62, docking of end 108 (which includes an opening 108a therein) with instrument dock 64 allows the transmission of light to tip 104 of threading device 100. In another embodiment other types of lighting can be used. For example, LED, incandescent, fluorescent and other light sources can be used.

It will be understood that, eyelet 102 is used to secure the suture 150. Eyelet 102 can be located anywhere along threading device 100.

In use, threading device 100 (and suture 150) are inserted through the various skin ports 80 and the support matrix 200 is weaved and created.

Figure 15:
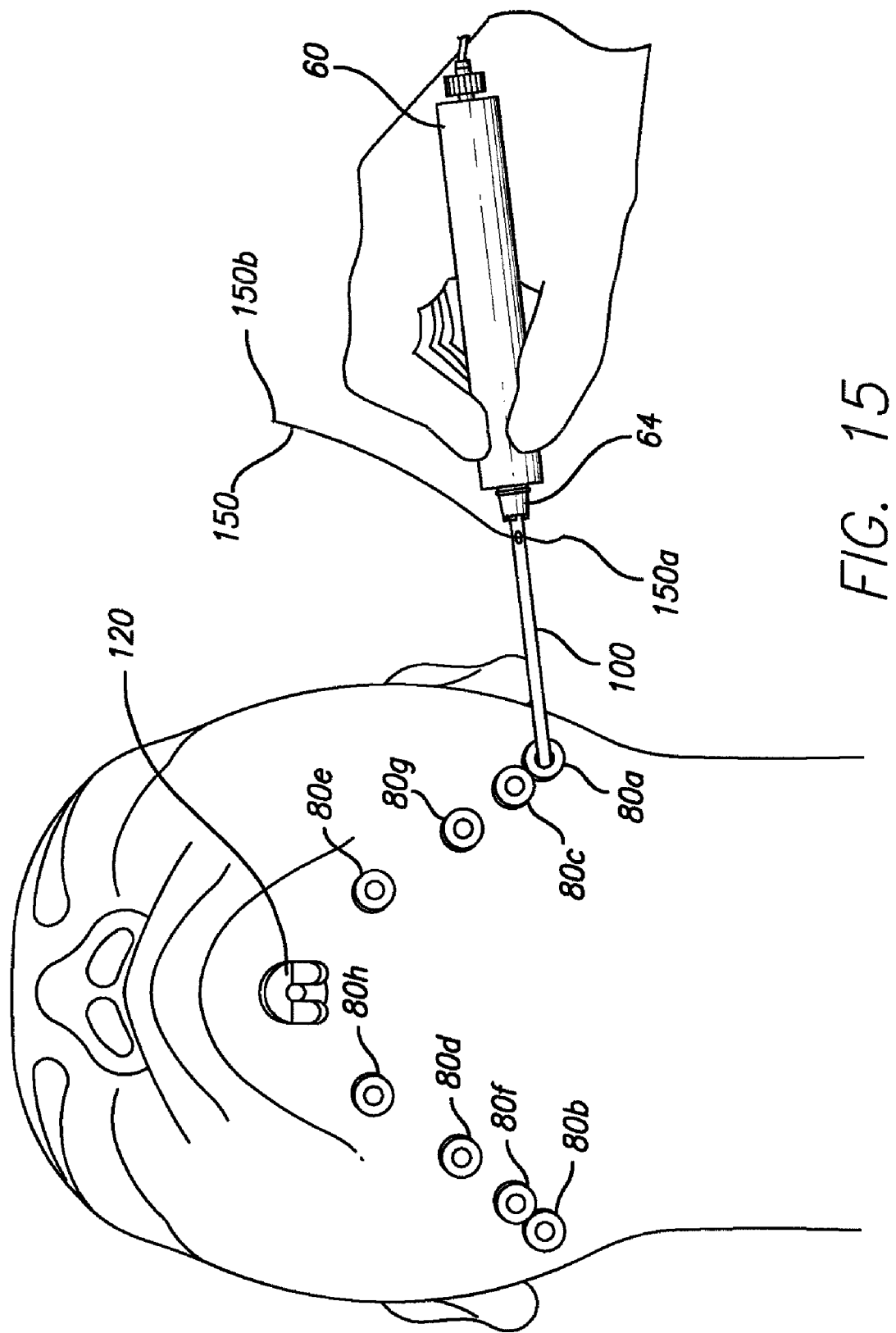
FIG. 15 is a view of the threading device of FIG. 13 being used on a patient.

An exemplary construction of a support matrix 200 will now be described. For example, as shown in FIG. 15, after first end 150a of the suture 150 is connected to eyelet 102, the handset 60 is grasped by the surgeon and the threading device is inserted through a first skin port 80a. The lighted tip 104 of threading device 100 illuminates the work area and transilluminates through the skin allowing the surgeon to determine the proper placement of the support matrix 200 and the location of the tip 104. As described above, in a preferred embodiment, port 80 is clear for aiding in the passage of the threading device 100. In other words, when the tip 104 of threading device 100 gets close to port 80 it will transilluminate.

Figure 16:
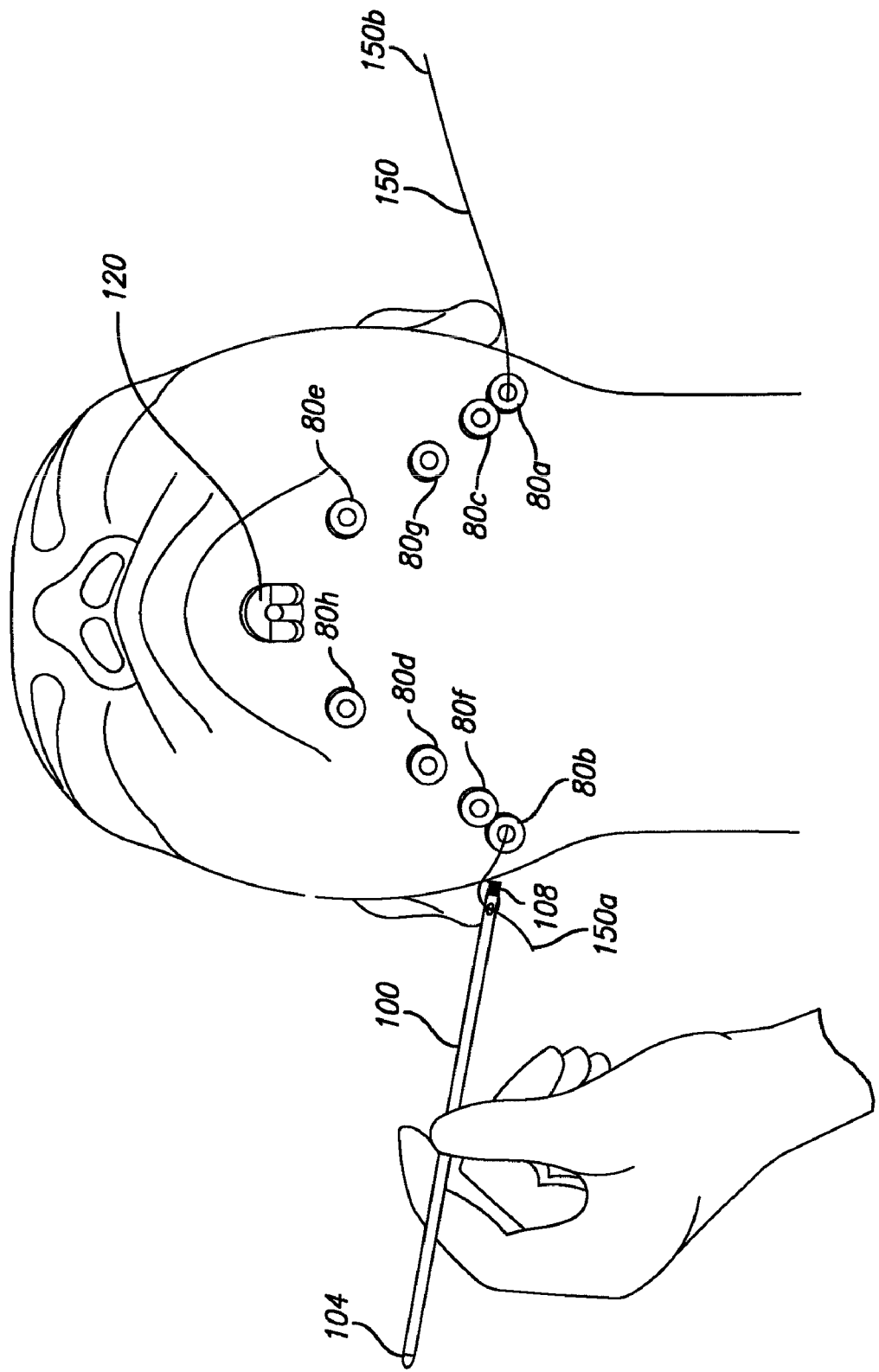
FIG. 16 is another view of the threading device of FIG. 13 being used on a patient.
Figure 17:
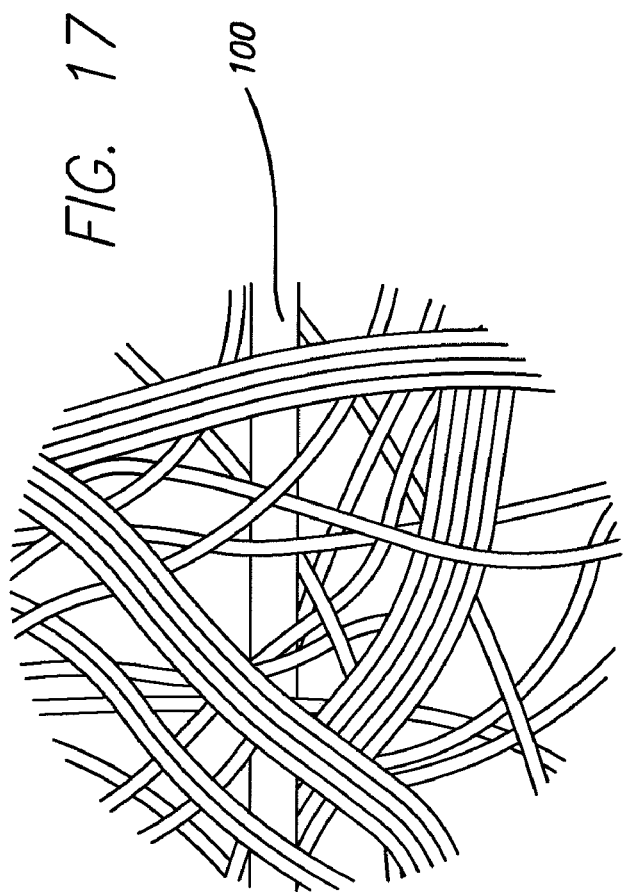
FIG. 17 illustrates the threading device of FIG. 13 passing through the subcutaneous facial ligaments and neurovascular structures.

The threading device 100 is preferably long enough that it can be threaded from one side of the jaw line to the other such that the tip 104 is brought out through a second skin port 80b on the opposite side of the jaw from which it was inserted. At this point, the tip 104 is grasped by the surgeon and the suture 150 is pulled through the area under the neck. Then the threading device 100 is disconnected from the handset 60 allowing the threading device 100 and the suture 150 to be pulled through the second skin port 80b, as is shown in FIG. 16.

The threading device 100 is then turned and reconnected to the handset 60 and is then reinserted through second skin port 80b and is passed subcutaneously to the contralateral side exiting through third skin port 80c. The threading device 100 is once again disconnected from the handset 60 and is reconnected after the threading device and suture 150 are pulled through third skin port 80c.

Next, the threading device 100 is turned and reconnected to the handset 60 and is then reinserted through third skin port 80c and is passed subcutaneously to the contralateral side exiting through fourth skin port 80d. At this point, the threading device 100 is once again disconnected from the handset 60 and is reconnected after the threading device and suture 150 are pulled through fourth skin port 80d.

The threading device 100 is then turned and reconnected to the handset 60 and is then reinserted through fourth skin port 80d and is passed subcutaneously to the contralateral side exiting through fifth skin port 80e. At this point, the threading device 100 is once again disconnected from the handset 60 and is reconnected after the threading device and suture 150 are pulled through fifth skin port 80e.

Next, the threading device 100 is turned and reconnected to the handset 60 and is then reinserted through fifth skin port 80e and is passed subcutaneously to the midline sub-mental access site which preferably includes a threaded skin port 120 (described more fully hereinbelow). The threading device 100 and first end 150a of suture 150 are pulled through the threaded skin port 122 and the threading device is disconnected from the handset 60. The first end 150a of suture 150 is then cut from and/or untied from the threading device 100.

Now, the second end (or distal end) 150b of suture 150, which is extending from first skin port 80a is secured to the eyelet 102 of the threading device 100 and the threading device 100 is connected to the handset 60. The handset 60 is grasped by the surgeon and the threading device is inserted through the first skin port 80a and is passed subcutaneously to the contralateral side exiting through sixth skin port 80f. At this the handset 60 and is reconnected after the threading device and suture 150 are pulled through sixth skin port 80f.

Next, the threading device 100 is turned and reconnected to the handset 60 and is then reinserted through sixth skin port 80f and is passed subcutaneously to the contralateral side exiting through seventh skin port 80g. At this point, the threading device 100 is once again disconnected from the handset 60 and is reconnected after the threading device and suture 150 are pulled through seventh skin port 80g.

The threading device 100 is then turned and reconnected to the handset 60 and is then reinserted through seventh skin port 80f and is passed subcutaneously to the contralateral side exiting through eighth skin port 80h. At this point, the threading device 100 is once again disconnected from the handset 60 and is reconnected after the threading device and suture 150 are pulled through eighth skin port 80h.

Next, the threading device 100 is turned and reconnected to the handset 60 and is then reinserted through eighth skin port 80h and is passed subcutaneously to the threaded skin port 120 at the midline sub-mental access site. The threading device 100 and second end 150b of suture 150 are pulled through the threaded skin port 120 and the threading device is disconnected from the handset 60.

As will be understood by those skilled in the art, the tube 84 on the skin ports 80 is long enough that when the threading itself by encircling the facial retaining ligaments during the procedure described above. Preferably, each time the threading device 100 and suture 150 are passed through a port 80, the suture is secured on the facial retaining ligaments, thereby creating an anchor or pivot point.

It will be understood that the number of access sites 14, ports 80 and/or passes, etc. described above are merely exemplary and any number can be used in the presently described procedure, as required by the particular surgery.

Transcutaneous light transmission from the tip 104 of the threading device 100 gives feedback allowing the surgeon to determine the location of the tip 104 as the support matrix 200 is weaved and created. This feedback allows the placement of each individual strand relative to areas of needed support. This allows placement of the suture strands 150 adjacent to the muscle, deep to the skin and fat layers.

Preferably, in each port 80, the end of the tube 84 that is associated with the flange 82 has a beveled or tapered edge 84a, which helps prevent the tip 104 of the threading device 100 from catching inside the tunnel 86, during insertion.

In another embodiment, two threading devices 100 that are each connected to an opposite end of the suture 150 can be used. In this embodiment the first threading device 100 does not have to be disconnected from the end of the suture 150 before the second end of the suture 150 is threaded through the skin. In yet another embodiment, the suture 150 can come in a kit with two disposable threading devices 100 attached to the opposite ends 150a and 150b. After forming the matrix 200, the threading devices 100 can be cut from the suture 150 and then the suture can be tied.

Figure 22:
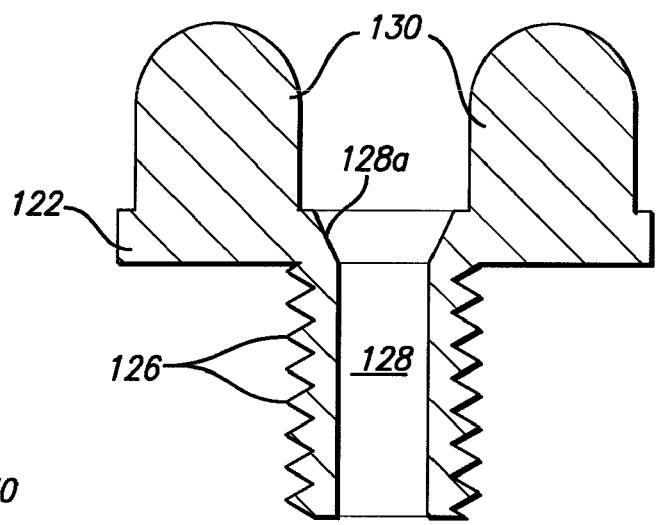
FIG. 22 is a sectional side elevational view of the threaded skin port of FIG. 21.
Figure 23:
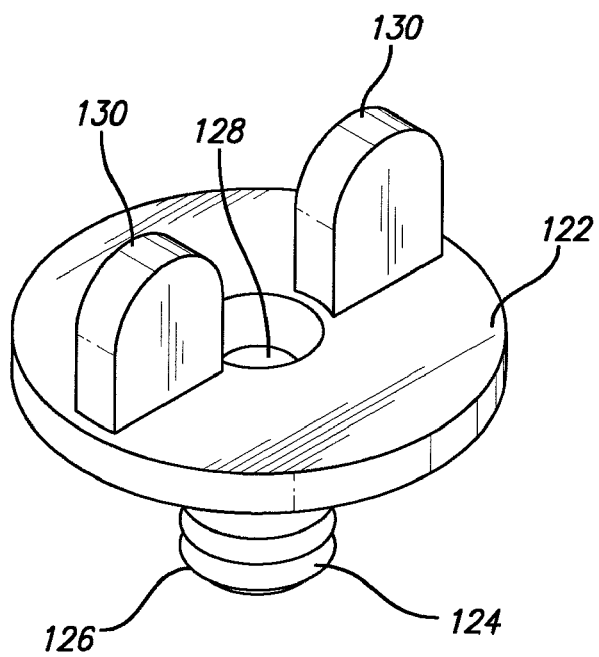
FIG. 23 is a perspective view of the threaded skin port of FIG. 21.

FIGS. 19-23 show the threaded skin port 120 used for the midline sub-mental access site. The threaded skin port 120 is inserted at the same time as the skin ports 80 described above. However, this is not a limitation on the present invention. The port 120 includes a flange 122 having a tube 124 extending therefrom. The tube 124 is preferably threaded 126. As is shown in FIG. 22, the tube 124 and flange 122 cooperate to define a tunnel 128 therethrough. In a preferred embodiment, the portion of the tunnel 128 in the flange 122 includes a beveled or tapered edge 128a.

In a preferred embodiment, the port 120 includes a pair of handle portions 130 extending upwardly from the flange 122 that aid the surgeon in threading the port 120 into the midline sub-mental access site. However, the handle portions 130 are not a limitation on the present invention and can be omitted. It will be understood that any skin port that allows access through the skin is within the scope of the present invention. For example, skin port 80 or something similar can be used at the midline sub-mental access site. In another embodiment, port 120 can be used at access site 14. In a preferred embodiment, port 120 is clear for aiding in the passage of the threading device 100. In other words, when the tip 104 threading device 1 gets close to the port 120 it will transilluminate.

In use, the tube 124 is inserted into the midline sub-mental access site. The handle portions 130 are grasped and the port 120 is turned so that the threads 126 are threaded into the skin until the bottom surface of the flange 122 rests against the outer surface of the skin.

In another embodiment, a port similar to skin port 80 described above, but somewhat modified can be used for mid-line access. In this embodiment, the flange includes a threaded interior that engages the threads on the exterior of the tube. The distal ends of the folding members are connected to a ring that is not internally threaded. This ring allows the tube to rotate therein, but (because it is not internally threaded) does not cause the ring to ride up the threads of the tube. The opposite ends of the folding members are connected to the flange.

With this configuration, when the tube is rotated (preferably by engagement with the handset or with a surgeon's fingers), the threaded engagement of the exterior of the tube with the interior of the flange causes the tube to move outwardly (with respect to the interior of a patient's body). This action causes the folding members to fold at the crease. In use with a patient, in the folded position, the proximal end of the tube is located outside of the patient's body, and the distal end has moved closer to the flange than it was in the unfolded position.

Figure 18:
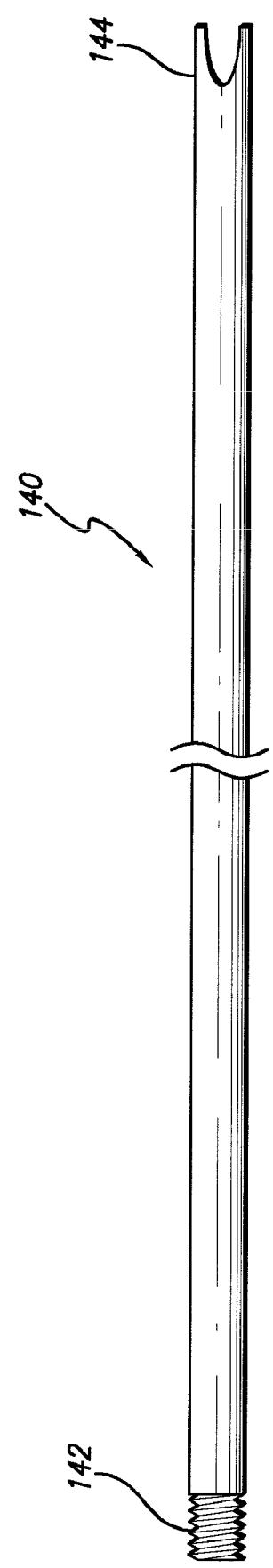
FIG. 18 is a side elevational view of a knot positioning implement in accordance with a preferred embodiment of the present invention.
Figure 19:
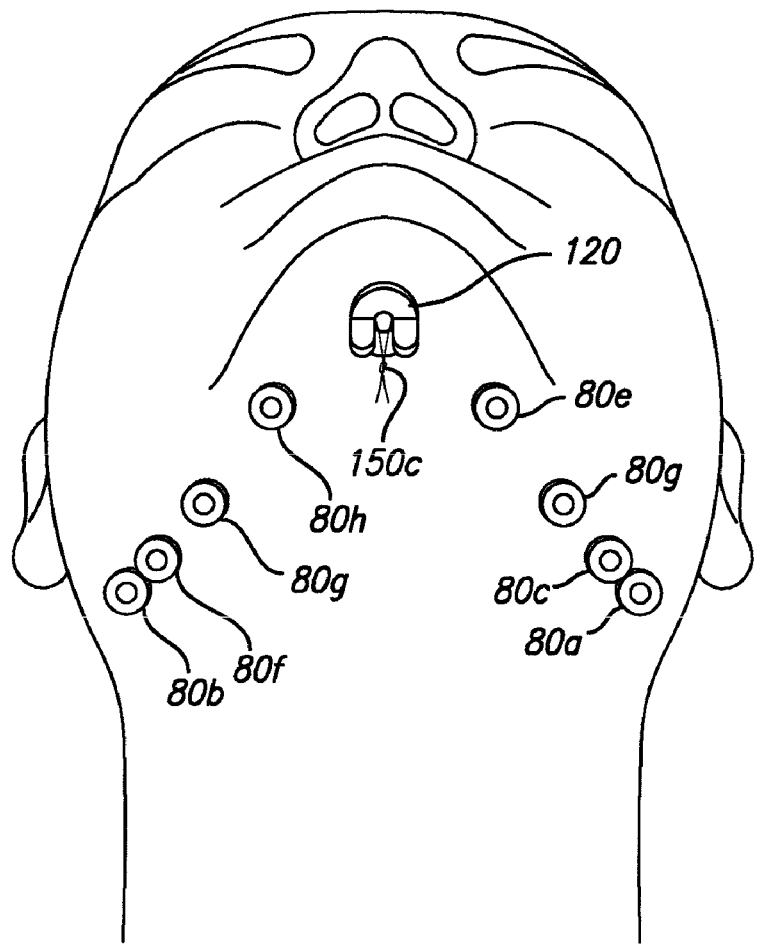
FIG. 19 is a view of a patient with a threaded skin port placed in the midline sub-mental access site and a suture knot extending therethrough.
Figure 20:
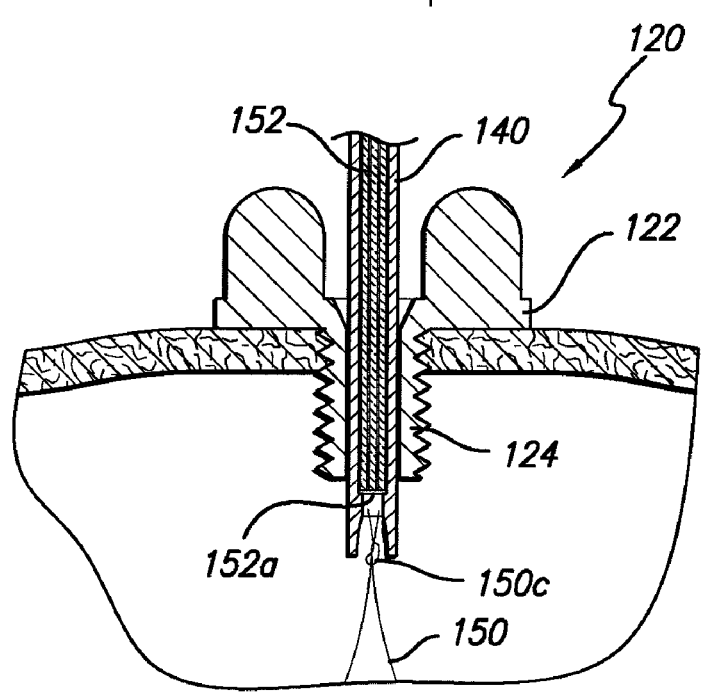
FIG. 20 is a cross-sectional view of the knot positioning implement of FIG. 15 pushing the knot through the threaded skin port and under a patient's skin.
Figure 21:
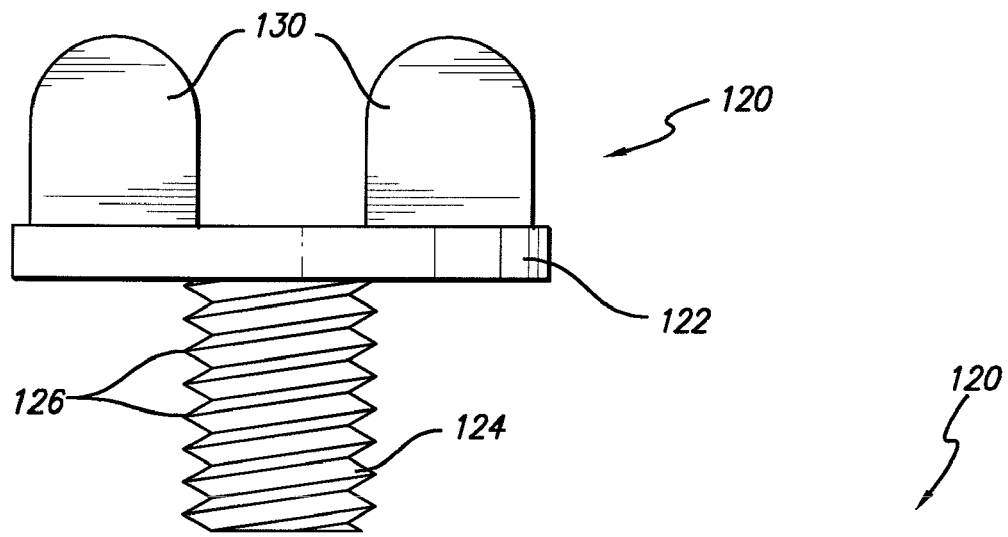
FIG. 21 is a side elevational view of a threaded skin port in accordance with a preferred embodiment of the present invention.

With reference to FIGS. 18-20, a knot positioning implement 140 is shown and described. After both ends 150a and 150b of the suture 150 are threaded and the support matrix 200 has been created, the two suture ends 150a and 150b are brought out through the midline sub-mental access site (through port 120), as is shown in FIG. 19. A single throw knot 150c is placed (it will be understood that the type of knot is not a limitation on the present invention) and the knot positioning implement 140 is utilized to set the knot 150c.

One end 142 of the knot positioning implement 140 (which is preferably threaded) docks with the handset 60 and the other end 144 is forked. The forked end 144 is used to push the knot 150c through the tunnel 128 of threaded skin port 120 and under the skin. In a preferred embodiment, the knot positioning implement 140 includes a fiber optic core 152 and an opening 152a through which light is transmitted to illuminate the work area when placing the knot 150c.

After the knot 150c has been pushed through the threaded port 120, threaded port 120 is twisted out of the access site and the other skin ports 80 are removed using the handset 60. To do this, the male connector 68 is inserted into the port 80 so that the ridge 68a snaps into the indented ring 82a and the teeth 68b and 82b engage one another. The handset 60 is then twisted, thereby turning tube 84 and causing the internally threaded ring 90b to travel back down threads 88 and unfolding folding the folding members 90a. In another embodiment, the ports 80 can be removed by hand.

After atraumatic removal of the ports 80 and 120, steristrips are then placed as desired and a neck compression garment is fitted onto the patient. See FIG. 25 for the final configuration of the exemplary support matrix 200.

Figure 24:
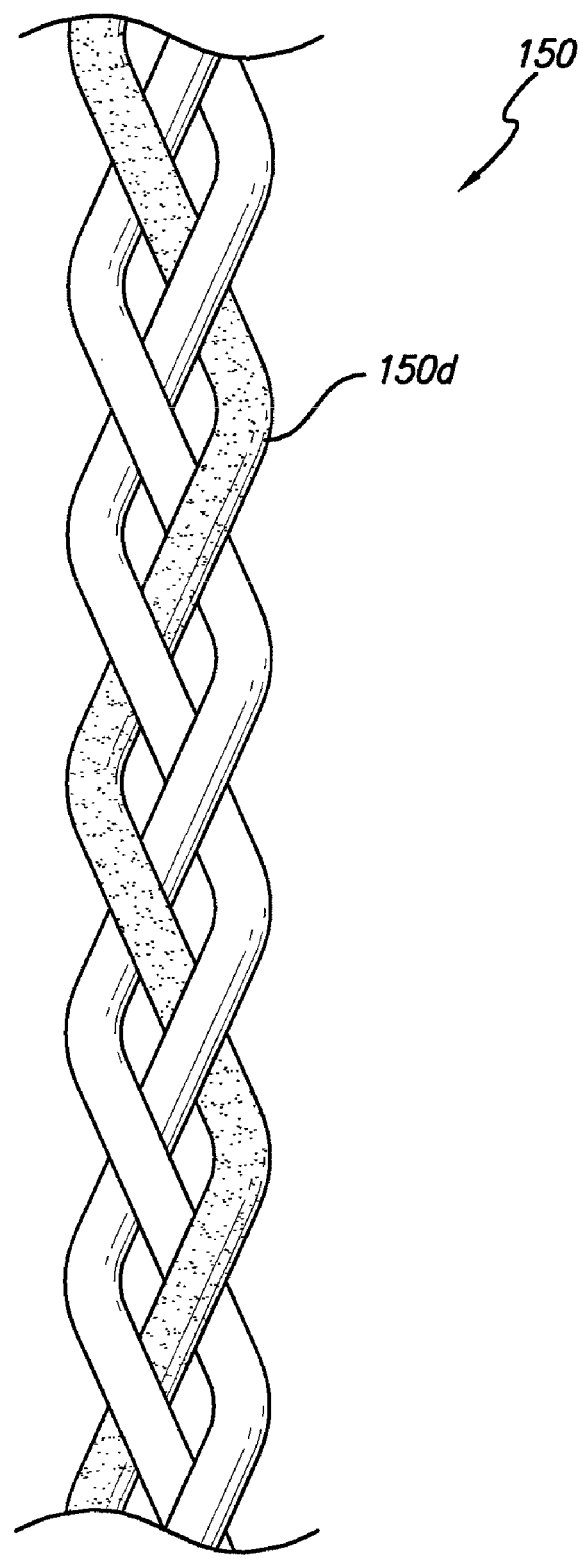
FIG. 24 is a side elevational view of a fiberoptic suture in accordance with a preferred embodiment of the present invention.

In a preferred embodiment, the suture that is used in the procedure is a 4.0 braided polyester suture. In a more preferred embodiment, as shown in FIG. 24, the suture design contains at least one fiberoptic strand 150d intertwined with the non-fiberoptic strands. The suture 150 is braided as is known in the art with one, two or three fiberoptic strands and one or two non-fiberoptic strands, as is desired. This aids in the transillumination of the suture 150 to check subcutaneous placement after the suture 150 has been placed. The fiberoptic strand 150d will illuminate when the handset 60 fiberoptic light coupled with the knot placement implement 140 is approximated to the suture during tying. Light transmitted to the suture allows the surgeon to visualize placement of the support matrix 200 as it is secured. The non-fiberoptic strands can be made of any material known in the art, such as nylon, polypropylene, or other non-absorbable material.

At any point during the creation of the support matrix 200, suture placement can be confirmed by placing the handset 60 (or any light source) at one of the ends 150a or 150b of the suture 150, thereby transmitting light down the fiberoptic strand 150d to check placement of the suture 150.

The illumination of the suture pathway allows the surgeon to determine the location of the suture. Overall, suture illumination gives the surgeon feedback relating to the anatomical movement of each pivot point.

It will be appreciated by those skilled in the art that the fiberoptic suture can be utilized in all areas of surgery or other materials where a lit binding material is needed, and not just in the technique described herein. In another embodiment, the threading device may be a straight or curved needle. Application of light energy during a surgical procedure will confirm suture placement and accuracy. Application of light postoperatively could allow surgeons to understand the evolution of suture placement related to time and aging.

In an alternative embodiment, the neck skin can be elevated from the platysma muscle via an incision similar to that used in the standard procedure discussed above to allow the surgeon to visualize the operative field and then the suture matrix can be placed through the ports 80 and access sites 14.

It is contemplated that the above described instruments can be sold in kits. For example, a kit with all or any combination of the instruments, including the tape 10, a marking pen, lancet 40, handset 60, skin ports 80, threading device 100, threaded skin port 120, knot positioning implement 140 and suture 150 can be sold.

The embodiments described above are exemplary embodiments of the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A method of creating a suture support matrix under the skin of a person, the method comprising the steps of
   a. connecting a threading device to the first end of a suture, wherein the threading device includes an elongated main body portion having first and second opposite ends, wherein the second end of the elongated main body portion is connected to the first end of the suture,
   b. inserting the threading device through a first opening in the skin,
   c. pulling the threading device through a second opening in the skin,
   d. reinserting the threading device through the second opening in the skin,
   e. pulling the threading device through a third opening in the skin,
   f. reinserting the threading device through the third opening in the skin,
   g. pulling the threading device through a fourth opening in the skin,
   h. disconnecting the threading device from the first end of the suture,
   i. connecting a threading device to the second end of the suture,
   j. inserting the threading device through the first opening in the skin,
   k. pulling the threading device through a fifth opening in the skin,
   l. reinserting the threading device through the fifth opening in the skin,
   m. pulling the threading device through the fourth opening in the skin,
   n. disconnecting the threading device from the second end of the suture, and
   o. tying the first and second ends of the suture into a knot.

2. The method of claim 1 wherein the threading device connected to the first and second ends of the suture is the same threading device.

3. The method of claim 1 wherein the threading device connected to the first end of the suture is different from the threading device connected to the second end of the suture.

4. The method of claim 1 wherein the main body portion includes an eyelet defined therethrough, and wherein the suture is connected to the main body portion via the eyelet.

5. The method of claim 4 wherein the second end of the main body portion includes a threaded portion.

6. The method of claim 5 wherein the first end of the main body portion includes a blunt tip.

7. The method of claim 4 further comprising the step of disconnecting the first end of the suture from the eyelet after pulling the thread through the fourth opening in the skin and connecting the second end of the suture to the eyelet.

8. The method of claim 1 wherein the first, second, third, fourth and fifth openings include skin ports inserted therein through which the threading device is inserted.

9. The method of claim 6 wherein the threading device includes a lighted tip.

10. The method of claim 9 wherein the threading device includes a fiberoptic core that illuminates the tip.

11. The method of claim 1 wherein the threading device is connected to a handset before being inserted through the first opening in the skin, and wherein the threading device is disconnected from the handset after at least a portion of the threading device has been pulled through the second opening in the skin.

12. The method of claim 11 wherein the threading device is connected to a handset before being inserted through the first opening in the skin, wherein the threading device is disconnected from the handset after at least a portion of the threading device has been pulled through the second opening in the skin, and wherein the handset includes a fiberoptic core that illuminates a fiberoptic core in the threading device.

* * * * *